United States Patent
Chang et al.

(10) Patent No.: US 8,106,219 B2
(45) Date of Patent: Jan. 31, 2012

(54) ORGANIC COMPOUND AND ORGANIC DYE USED IN DYE-SENSITIZED SOLAR CELL

(75) Inventors: Shu-Mei Chang, Taipei (TW); Yu-Cheng Chang, Taichung (TW); Chi-Ming Lan, Yangmei Township, Taoyuan County (TW)

(73) Assignee: National Taipei University of Technology, Taipei (TW)

( * ) Notice: Subject to any disclaimer, the term of this patent is extended or adjusted under 35 U.S.C. 154(b) by 32 days.

(21) Appl. No.: 12/702,409

(22) Filed: Feb. 9, 2010

(65) Prior Publication Data

US 2010/0222596 A1 Sep. 2, 2010

(30) Foreign Application Priority Data

Aug. 28, 2009 (TW) .............................. 98128970 A (51) Int. Cl.
*C07D 495/04* (2006.01)

(52) U.S. Cl. .......................................... 549/32
(58) Field of Classification Search ................. None
See application file for complete search history.

(56) References Cited

OTHER PUBLICATIONS

Yu-Cheng Chang, "Synthesis of Novel Organic Dyes for Dye Sensitized Solar Cells", Feb. 2009, Institute of Organic and Polymeric Materials, National Taipei University of Technology.

*Primary Examiner* — Kamal Saeed
*Assistant Examiner* — Nyeemah A Grazier
(74) *Attorney, Agent, or Firm* — IPR Works, LLC (57) ABSTRACT

A kind of organic compound and organic dye used in dye-sensitized solar cell thereof. In the present invention, we synthesize a series of novel organic compounds with the structure of donor-conjugated chain-acceptor (D-π-A). The electron donor and acceptor groups, for example, are arylamine and cyanoacrylic acid, respectively. These novel organic compounds can be applied to the material of dye layer in the dye-sensitized solar cell (DSSC).

6 Claims, 1 Drawing Sheet

FIG. 1

ORGANIC COMPOUND AND ORGANIC DYE USED IN DYE-SENSITIZED SOLAR CELL

BACKGROUND OF THE INVENTION

1. Field of the Invention

The present invention relates to a structure of organic compound. More particularly, the present invention relates to a kind of organic compound and organic dye used in dye-sensitized solar cell thereof.

2. Description of Related Art

Since 1910, the scientists have begun to study the function of sensitized dye. But there were more focuses on looking for the photosensitized redox reactions at that time. After 1950, there were studies on the applications of the dye polymerization and sensitized reactions of modified dye on the surface of the catalytic materials.

From 1960~70, the sensitized dye was applied to the solar cell but the conversion efficiency were not good at that time. Until 1976, Tsubomura (Japan) published that the porous ZnO was utilized to be the working electrode of dye-sensitized solar cell and got 2.5% conversion efficiency. After that, the dye-sensitized solar cell became a research direction of the novel solar cell but the whole efficiency can not be highly improved.

Until 1991, M. Grätzel (Switzerland) developed a high efficiency and low-cost dye-sensitized solar cell. He utilized the nano-crystal $TiO_2$ to be the electrode, the ruthenium complex compound to be the sensitized dye, the iodine solution ($I^-/I_3^-$) to be the electrolyte and the conductive glass coated with platinum to be the electrode. Because the nano-crystal $TiO_2$ can absorb more dyes to increase the absorption area of incident light and the ideal light absorbability of the dyes, the conversion efficiency of dye-sensitized solar cell were improved.

SUMMARY OF THE INVENTION

Accordingly, the present invention provides a kind of organic compound, which has novel structures.

And, the present invention is directed to a kind of organic dye used in dye-sensitized solar cell and the organic dye has the said novel structures for providing the high efficiently solar cells of commercial pursuits.

The present invention provides a kind of organic compound and organic dye used in dye-sensitized solar cell thereof, comprising a structure of the following formula (I):

(I)

According to an embodiment of the present invention, wherein X or Y of the formula (I), for example, is independently selected from the following group:

Since modifying the end of donor on the organic compound of the formula (I), the present invention improves the efficiency of electron resupply.

Moreover, the modified end of donor can also improve UV absorbance of the organic dye used in dye-sensitized solar cell in the present invention. Based on the current record, the modifications are almost on the linker of the dye. There is no design of the dye like the present invention.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE PREFERRED EMBODIMENTS

Reference will now be made in detail to the present embodiments of the invention, examples of which are illustrated in the accompanying drawings. Wherever possible, the same reference numbers are used in the drawings and the description to refer to the same or like parts.

The present invention provides a kind of organic compound and organic dye used in dye-sensitized solar cell thereof. In the present invention, the kind of organic compound comprises a structure of the following formula (I):

(I)

wherein W, for example, is selected from the following group: hydrogen atom (H), $C_4H_9$, $C_mH_{2m+1}$ (m=1~30), $OC_pH_{2p+1}$ (p=1~30), $SC_pH_{2p+1}$ (p=1~30), $N(C_pH_{2p+1})_2$ (p=1~30), $CH_2[OC_2H_4]_nOCH_3$ (n=1~30), $[OC_2H_4]_qOCH_3$ (q=1~30), or  ;

A, for example, is selected from the following group:

or

;

B, for example, is selected from the following group:

,  ,

,  ,

,  ,

-continued or

;

wherein L on B of the formula (I), for example, is selected from oxygen atom (O), sulfur atom (S), selenium (Se).

The X or Y of the formula (I), for example, is independently selected from the following group:

or;

wherein D, for example, is selected from carbon atom (C) or silicon atom (Si).

The $R_1$~$R_{25}$, $R_{49}$~$R_{78}$ or Z, for example, is independently selected from the following group: hydrogen atom (H), $C_4H_9$, $C_mH_{2m+1}$ (m=1~30), $OC_pH_{2p+1}$ (p=1~30), $SC_pH_{2p+1}$ (p=1~30), $N(C_pH_{2p+1})_2$ (p=1~30), $CH_2[OC_2H_4]_nOCH_3$ (n=1~30) or $[OC_2H_4]_qOCH_3$ (q=1~30).

The $W_1$, $W_2$ or $W_3$ on A of the formula (I), for example, is independently selected from hydrogen atom (H), lithium (Li), sodium (Na) or tetra-alkyl ammonium and the R on A of the formula (I), for example, is comprised by $C_mH_{2m+1}$ (m=1~30).

For a simple and clear statement, the following organic compounds, B11, B12, B13, B14 and B15 are the embodiments, for example, to illustrate the formula (I).

When W is

$W_1$ on A is H, L on B is S, $R_{51}$ and $R_{52}$ are H, $R_1$ and $R_2$ on X are H, $R_{14}$ and $R_{15}$ on Y are H, and Z is $OC_pH_{2p+1}$ (p=6), the formula (I) has the following structure of compound B11:

When W is

$W_2$ on A is H, L on B is S, $R_{51}$ and $R_{52}$ are H, $R_1$ and $R_2$ on X are H, $R_{14}$ and $R_{15}$ on Y are H, and Z is $OC_pH_{2p+1}$ (p=6), the formula (I) has the following structure of compound B12:

When W is

$W_3$ on A is H, R on A is $C_mH_{2m+1}$ (m=8), L on B is S, $R_{51}$ and $R_{52}$ are H, $R_1$ and $R_2$ on X are H, $R_{14}$ and $R_{15}$ on Y are H, and Z is $OC_pH_{2p+1}$ (p=6), the formula (I) has the following structure of the compound B13:

When W is

$W_1$ on A is H, $R_{56}$ and $R_{57}$ on B are H, $R_1$ and $R_2$ on X are H, $R_{16}$ and $R_{17}$ on Y are H, and Z is $OC_pH_{2p+1}$ (p=6), the formula (I) has the following structure of compound B14:

B14

Figure 1:
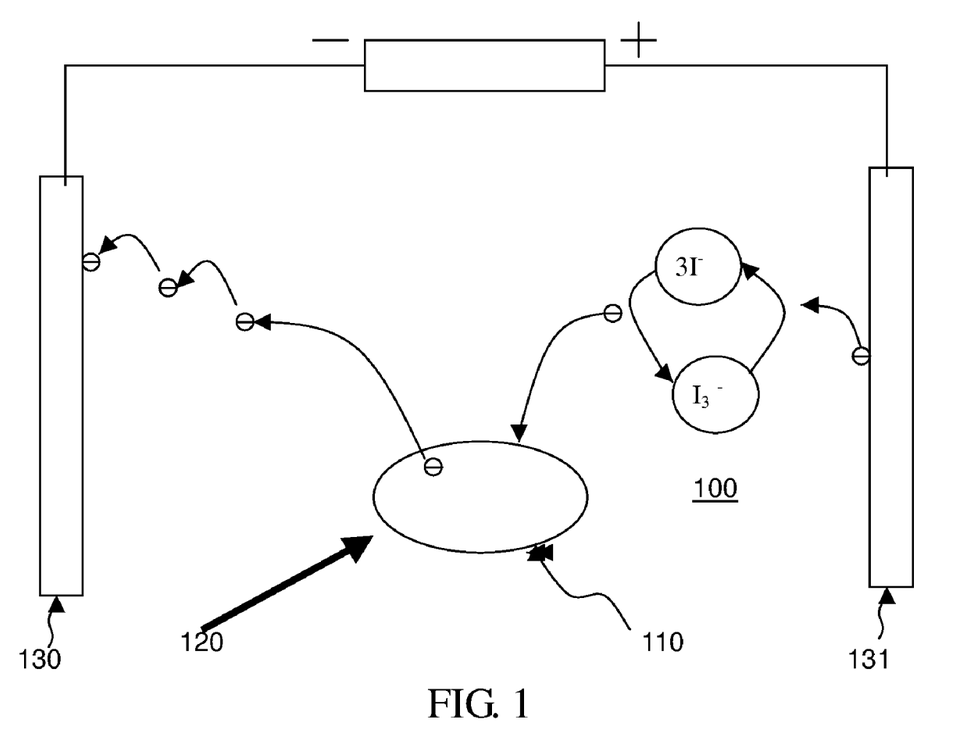
FIG. 1 is a schematic diagram illustrating the mechanism of the organic dye used in dye-sensitized solar cell according to one embodiment of the present invention.

When W is $C_mH_{2m+1}$ (m=6), $W_1$ on A is H, L on B is S, $R_{49}$ and $R_{50}$ are H, $R_1$ and $R_2$ on X are H, $R_{16}$ and $R_{17}$ on Y are H, and Z is $OC_pH_{2p+1}$ (p=6), the formula (I) has the following structure of compound B15:

trons transport to the cathode and then to the counter electrode 131. Finally, the electrons resupply to the organic dye 110 through the oxidation and reduction reactions of iodine ($3I^-/I_3^-$) in the electrolyte 100.

B15

The present invention provides a kind of organic compound and organic dye used in dye-sensitized solar cell thereof. In the present invention, the organic dye used in dye-sensitized solar cell comprises the structure of the formula (I). The mechanism of the organic dye used in the solar cell is depicted as the following FIG. 1.

FIG. 1 is a schematic diagram illustrating the mechanism of the organic dye used in dye-sensitized solar cell according to one embodiment of the present invention. Referring to FIG. 1, the organic dye 110 is lighted 120 and then the electrons transport from HOMO (Highest Occupied Molecular Orbital) to LUMO (Lowest Unoccupied Molecular Orbital) of the organic dye. And, the electrons transport to the $TiO_2$, coated on the electrode 130. Through the outside circuit, the elec- In summary, the present invention provides a kind of organic compound and organic dye used in dye-sensitized solar cell thereof. In the present invention, all variants of the formula (I) comprise the acceptor, whose functional group bonded to the semiconductor electrode, the donor, modified by a least one substituent, and the conjugate group, making conjugated linkages between the acceptor and the donor.

The present invention designs the organic compound structure of the formula (I) to have a modified end of donor. Since the structural characteristics, the organic compounds of the present invention easily generate the oxidation and reduction reactions with the electrolyte. Thereof, the efficiency of electron resupply to the organic dye can be improved by the present invention.

Moreover, the modified end of donor can also improve UV absorbance of the organic dye used in dye-sensitized solar cell in the present invention. Based on the current record, there is no design of the dye like the present invention.

It will be apparent to those skilled in the art that various modifications and variations can be made to the structure of the present invention without departing from the scope or spirit of the invention. In view of the foregoing descriptions, it is intended that the present invention covers modifications and variations of this invention if they fall within the scope of the following claims and their equivalents.

What is claimed is:

1. An organic compound, of formula (I):

wherein N represents a nitrogen atom;
W is

A is where $W_1$ represents a hydrogen atom;
B is where L represents a sulfur atom (S); $R_{51}$ and $R_{52}$ separately represent hydrogen atoms (H); and n=1;

wherein the —X—Y—Z group has a structure shown in the following:

2. An organic compound, which is an organic dye used in a dye-sensitized solar cell, of formula (I):

wherein W is

A is a group selected from:

where $W_1$, $W_2$, and $W_3$ on A of the formula (I) separately represent a hydrogen atom (H) and R on A of the formula (I) represents $C_mH_{2m+1}$ (m=1~30);

15

B is a group selected from:

where $R_{49}$, $R_{50}$, $R_{51}$, $R_{52}$, $R_{53}$, $R_{54}$, $R_{55}$, $R_{56}$, $R_{57}$, $R_{58}$, $R_{59}$, $R_{69}$, $R_{70}$, $R_{71}$, $R_{72}$, $R_{73}$, $R_{74}$, $R_{75}$, $R_{76}$ independently represent H or $C_mH_{2m+1}$ (m=1-30), L represents an oxygen atom (O), a sulfur atom (S), or a selenium atom (Se) and n represents an integer of 1-30; and

16

X and Y are moieties independently selected from a group consisting of the following:

where $R_1$~$R_{17}$ independently represent H or $C_mH_{2m+1}$ (m=1~30).

3. The organic compound according to claim 1, which is an organic dye used in a dye-sensitized solar cell and has the following structure B11:

4. The organic compound according to claim 2, having the following structure shown by B11:

5. The organic compound according to claim 2, having the following structure shown by B12:

6. The organic compound according to claim 2, having the following structure shown by B13:

* * * * *